(12) United States Patent
Scott et al.

(10) Patent No.: US 9,067,009 B2
(45) Date of Patent: Jun. 30, 2015

(54) REGULATING FLOW PATHS IN A MEDICAL INJECTION SYSTEM

(71) Applicant: ACIST MEDICAL SYSTEMS, INC., Eden Prairie, MN (US)

(72) Inventors: David Duane Scott, Minneapolis, MN (US); Tom H. Borlaug, Prior Lake, MN (US); Scott Jacob Soltis, Minneapolis, MN (US)

(73) Assignee: ACIST Medical Systems, Inc., Eden Prairie, MN (US)

( * ) Notice: Subject to any disclaimer, the term of this patent is extended or adjusted under 35 U.S.C. 154(b) by 141 days.

(21) Appl. No.: 13/750,724

(22) Filed: Jan. 25, 2013

(65) Prior Publication Data

US 2014/0213974 A1   Jul. 31, 2014

(51) Int. Cl.
  *A61M 1/00*   (2006.01)
  *F16K 31/00*   (2006.01)
  *A61M 5/142*   (2006.01)
  *A61M 39/22*   (2006.01)

(52) U.S. Cl.
  CPC .............. *A61M 5/142* (2013.01); *A61M 39/223* (2013.01); *A61M 39/22* (2013.01)

(58) Field of Classification Search
  USPC ............... 137/625.4, 625.41, 625.42, 625.43, 137/625.46; 604/32, 83, 248, 258; 251/292, 251/293, 296, 298
  See application file for complete search history.

(56) References Cited

U.S. PATENT DOCUMENTS

| | | | |
|---|---|---|---|
| 1,853,202 A * | 4/1932 | Catlin | 604/32 |
| 2,564,977 A * | 8/1951 | Hu | 604/32 |
| 3,048,192 A * | 8/1962 | Murphy, Jr. | 137/625.42 |
| 3,078,848 A * | 2/1963 | Milbert | 604/32 |
| 3,780,736 A * | 12/1973 | Chen | 604/32 |
| 4,593,717 A * | 6/1986 | Levasseur | 137/556.6 |
| 4,950,230 A | 8/1990 | Kendell | |
| 5,156,186 A | 10/1992 | Manska | |
| 5,443,453 A | 8/1995 | Schweitzer et al. | |
| 5,649,810 A | 7/1997 | Schweitzer et al. | |
| 6,880,808 B2 | 4/2005 | McPeak et al. | |
| 2006/0089603 A1 | 4/2006 | Truitt et al. | |

FOREIGN PATENT DOCUMENTS

EP     1754505 A1   2/2007
WO    03057070 A2   7/2003

OTHER PUBLICATIONS

International Search Report and Written Opinion for corresponding International Application No. PCT/US2013/075657, mailed May 22, 2014, 11 pages.

* cited by examiner

*Primary Examiner* — Manuel Mendez
(74) *Attorney, Agent, or Firm* — Fredrikson & Byron, P.A.

(57) ABSTRACT

A core, rotatably fitted within a body of a manifold assembly, includes a flow channel configured so that, when the core is rotated 360 degrees, fluid communication between ports of the body is only established by the channel at a first position, between first and second ports, and at a second position, between third and fourth ports. The channel may define an angle greater than 90 degrees and less than 180 degrees, preferably 120 degrees; and, the rotation, between first and second positions, may be approximately 180 degrees. In a medical injection system, the first and second ports are fill ports of the assembly, the first being coupled to a reservoir, and the second being coupled to a pump; and the third and fourth ports are injection ports of the assembly, the third being coupled to the pump, and the fourth being coupled to an injection line.

13 Claims, 4 Drawing Sheets

REGULATING FLOW PATHS IN A MEDICAL INJECTION SYSTEM

TECHNICAL FIELD

The present disclosure pertains to medical injection systems and more particularly to apparatus for regulating flow paths therein.

BACKGROUND

FIG. 1 is a perspective view of an exemplary medical injection system 100 (the ACIST CV$_i$® system) for delivering a contrast agent into a patient's vascular system for medical imaging. FIG. 1 illustrates a first fluid reservoir 132 for supplying a syringe-type positive displacement pump 130 of a pressurizing unit, via a fill tubing line 102, and an injection tubing line 104, which is coupled to pump 130 for injection of, for example, a radiopaque contrast agent, into a patient's vascular system via an inserted catheter (not shown) that may be coupled to a patient tubing line 122 at a connector 120 thereof. FIG. 1 further illustrates a second fluid reservoir 138 from which a diluent, such as saline, is drawn by a peristaltic pump 106 through yet another tubing line 128 that feeds into tubing line 122. A manifold valve 124 and associated sensor 114 control the flow of fluids into tubing line 122, from pump 130 and from tubing line 128.

Although not shown in FIG. 1, the syringe-type positive displacement pump of unit 130 includes a fill port and an injection port to which tubing lines 102 and 104, respectively are coupled. An apparatus that allows fluid to flow into pump 130, via fill tubing line 102, while blocking flow to injection tubing line 104, and then allows fluid to flow out from pump 130, via injection tubing line 104, while blocking flow to fill tubing line 104, is desired in order to prevent back flow through line 104 during filling, and back flow through line 102 during injection. Such an apparatus may be integrated into system 100 in the general area designated by reference numeral 125, and may be in the form of a stop cock-type manifold. Although various configurations of this type manifold apparatus are known in the art, there is a need for new and improved configurations of manifold assemblies for regulating flow paths in medical injection systems, for example, like system 100.

SUMMARY

Embodiments of the present invention are directed toward manifold apparatus that may be employed to regulate flow paths in a medical injection system. According to some embodiments, a flow control core is rotatably fitted within an inner perimeter surface of a body to form a manifold assembly, wherein the core includes a flow channel extending therethrough, and the body includes a first port extending from an opening located in a first quadrant of the inner perimeter surface, a second port extending from an opening located in a second quadrant of the inner perimeter surface, a third port extending from an opening located in a third quadrant of the inner perimeter surface, and a fourth port extending from an opening located in a fourth quadrant of the inner perimeter surface; the configuration of the flow channel is such that, when the core is rotated 360 degrees within the body, fluid communication between ports of the body is only established by the flow channel of the core in two positions: at a first position, between the first and second ports of the body, and at a second position, between the third and fourth ports of the body. Thus, fluid communication between any of the ports at any other position besides the first and second positions is prevented. The flow channel of the core may extend in two sections that define an angle which is greater than 90 degrees and less than 180 degrees, preferably 120 degrees. According to some preferred embodiments, the rotation of the core, between the first and second positions, is approximately 180 degrees.

In a medical injection system of the present invention, the aforementioned first and second ports are fill ports of the manifold assembly, wherein the first is coupled to a reservoir of fluid, for example, contrast agent, and the second is coupled to a fill port of a positive displacement pump; and the aforementioned third and fourth ports are injection ports of the manifold assembly, wherein the third is coupled to an injection port of the pump, and the fourth is coupled to an injection tubing line. The system preferably includes a drive member for rotating the flow control core of the manifold assembly, so that, according to some embodiments, the flow control core of the manifold assembly further includes an actuation member, which is engaged by drive member of the system. According to preferred embodiments, the manifold assembly is integrated into the medical injection system such that the fill ports (first and second ports) of the manifold assembly are located at a higher elevation than the injection ports (third and fourth ports).

BRIEF DESCRIPTION OF THE DRAWINGS

The following drawings are illustrative of particular methods and embodiments of the present disclosure and, therefore, do not limit the scope of the invention. The drawings are not to scale (unless so stated) and are intended for use in conjunction with the explanations in the following detailed description. Methods and embodiments will hereinafter be described in conjunction with the appended drawings, wherein like numerals denote like elements, and.

DETAILED DESCRIPTION

The following detailed description is exemplary in nature and is not intended to limit the scope, applicability, or configuration of the invention in any way. Rather, the following description provides practical illustrations for implementing exemplary methods and embodiments. Examples of constructions, materials and dimensions are provided for selected elements, and all other elements employ that which is known to those of skill in the field of the invention. Those skilled in the art will recognize that many of the examples provided have suitable alternatives that can be utilized.

Figure 1:
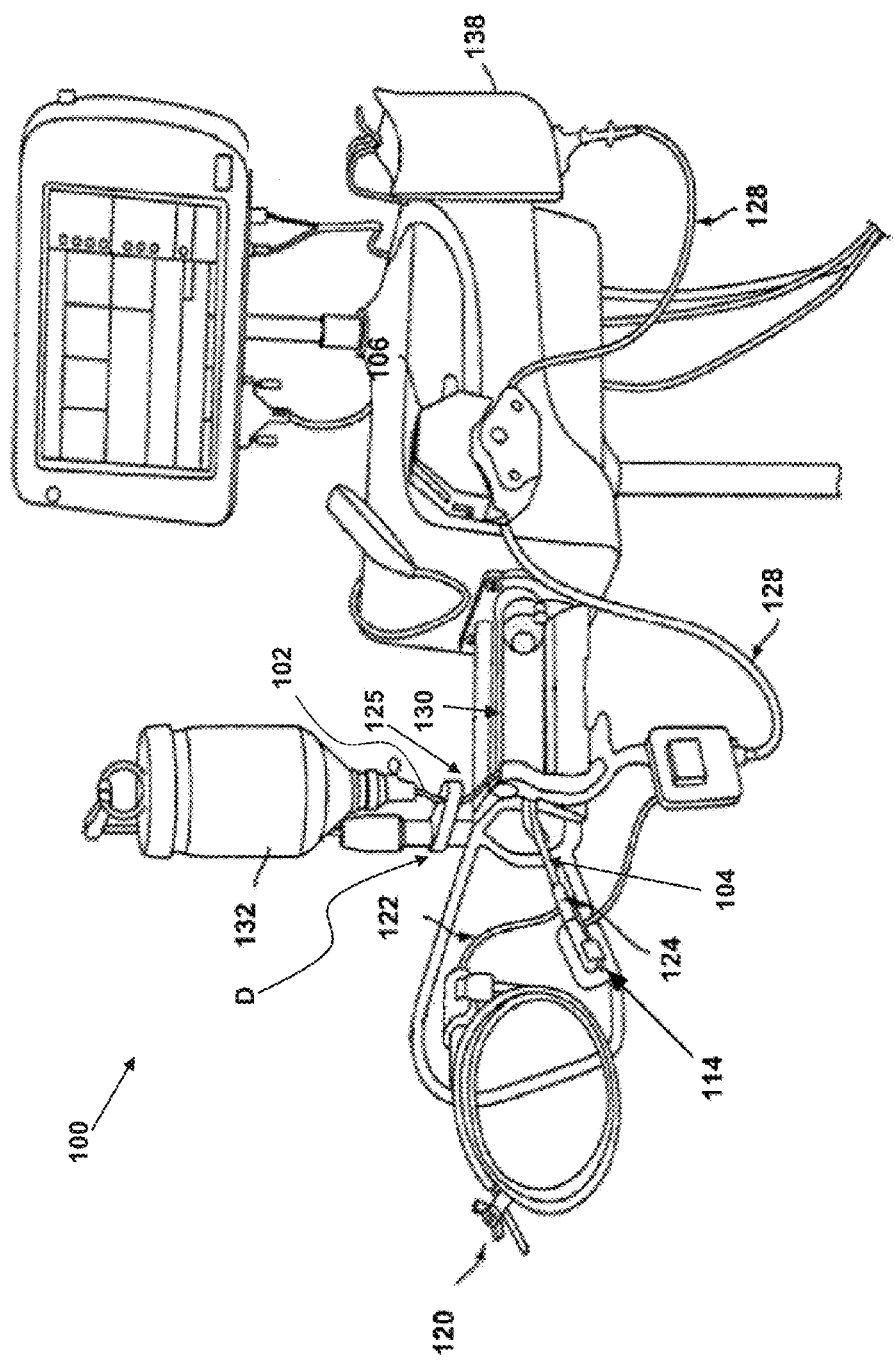
FIG. 1 is a perspective view of an exemplary medical injection system that may employ embodiments of the present invention.
Figure 2:
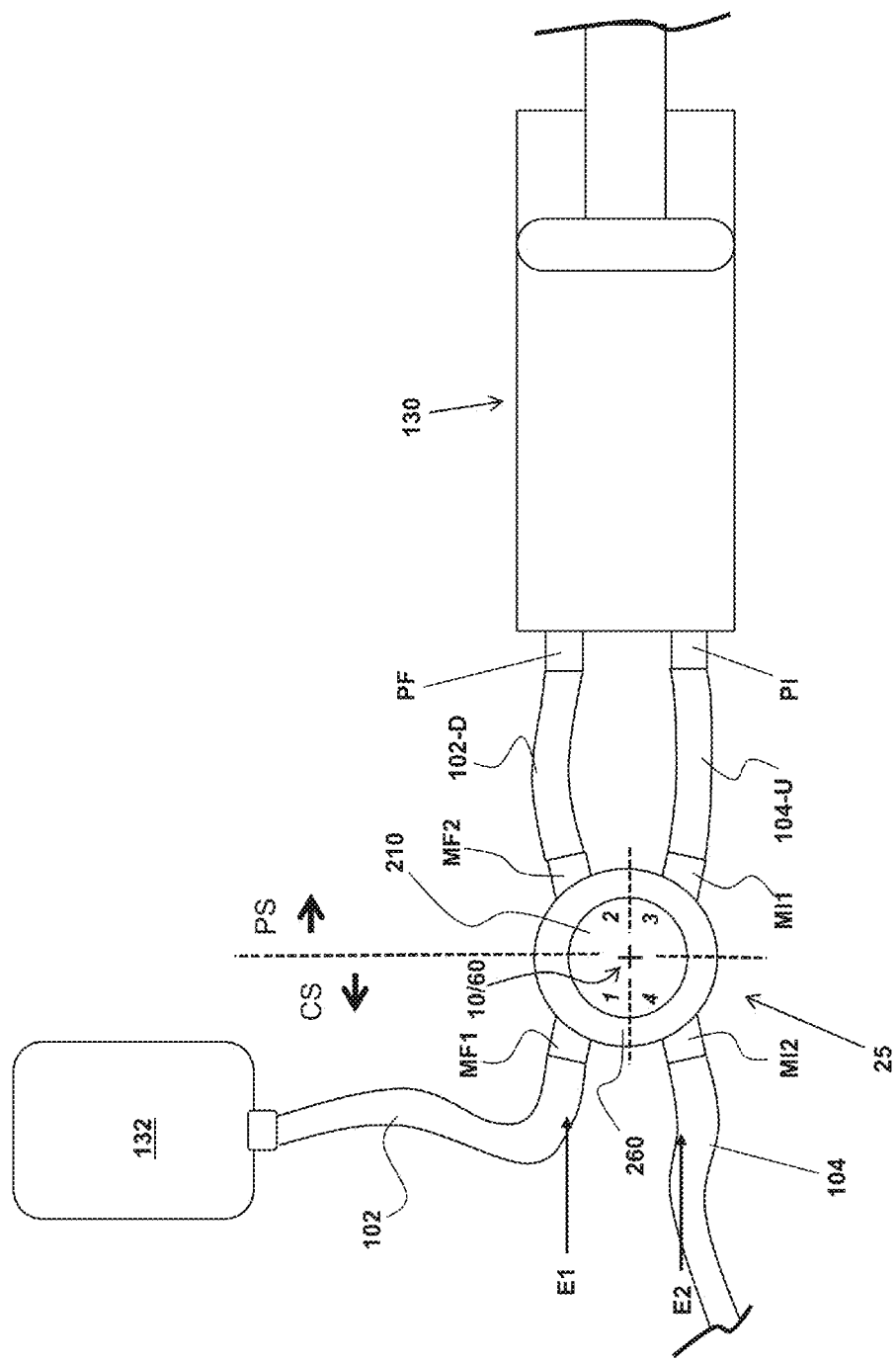
FIG. 2 is a schematic illustration of a manifold assembly coupled to a positive displacement pump, which may incorporated in the system of FIG. 1, according to some embodiments of the present invention.

FIG. 2 is a schematic illustration of a manifold assembly 25, which is coupled to positive displacement pump 130, for example, of system 100 (FIG. 1), according to some embodiments of the present invention. FIG. 2 illustrates manifold assembly 25 including a body 260 and a flow control core 210, which is fitted within an inner perimeter surface 36 (FIG. 3A) of body 260, such that a longitudinal axis 10 of core 210 is approximately aligned with a longitudinal axis 60 of body 260. FIG. 2 further illustrates manifold assembly 25 including a first fill port MF1, a second fill port MF2, a first injection port MI1 and second injection port MI2, all of which are formed in body 260. First fill port MF1 is shown coupled to fill tubing line 102 that extends from reservoir 132, as described above, and second fill portion MF2 is shown coupled to a fill port PF of pump 130, for example, via a downstream fill tubing line 102-D. With further reference to FIG. 2, first injection port MI1 is likewise coupled to an injection port PI of pump 130, via an upstream injection tubing line 104-U, and second injection port MI2 is coupled to injection tubing line 104, which as described above, extends to a terminal connector, for example, connector 120 of FIG. 1, for connection to a patient line or catheter. According to the illustrated embodiment core 210 is rotatable within body 260, and with reference to FIGS. 3A-B, core 210 includes a flow channel 31 extending therethrough, from a first opening 311 at an outer perimeter surface 32 thereof to a second opening 312 at the outer perimeter surface 32. According to the illustrated embodiment, outer perimeter surface 32 of core 210 seals against inner perimeter surface 36 of body 260, when core 210 is fitted/inserted therein, per arrow A (FIG. 3A), and the fitted core 210 is rotatable within body 260 between first and second positions, for example, positions P-1 and P-1 shown in the schematic of FIG. 4. Both core 210 and body 260 of manifold assembly 25 may be formed of any suitable material (e.g., plastic, stainless steel) by any suitable method known to those skilled in the art.

Figure 3B:
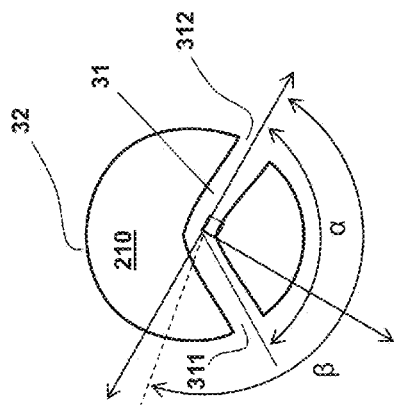
FIG. 3B is a cross-section view through section line A-A of FIG. 3A, according to some embodiments.
Figure 3C:
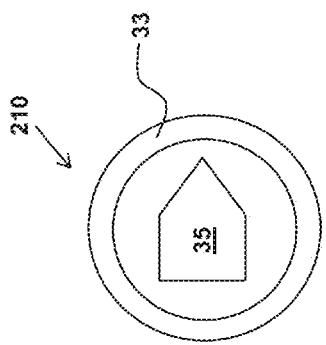
FIG. 3C is another view of a flow control core of the assembly shown in FIG. 3A.
Figure 3A:
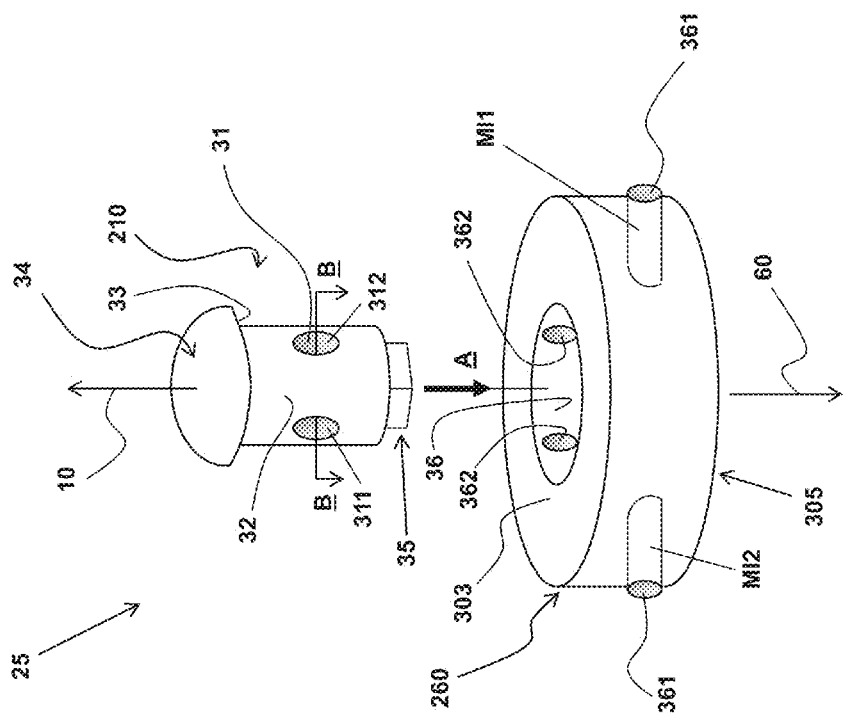
FIG. 3A is an exploded perspective view of a manifold assembly, according to some embodiments.
Figure 4:
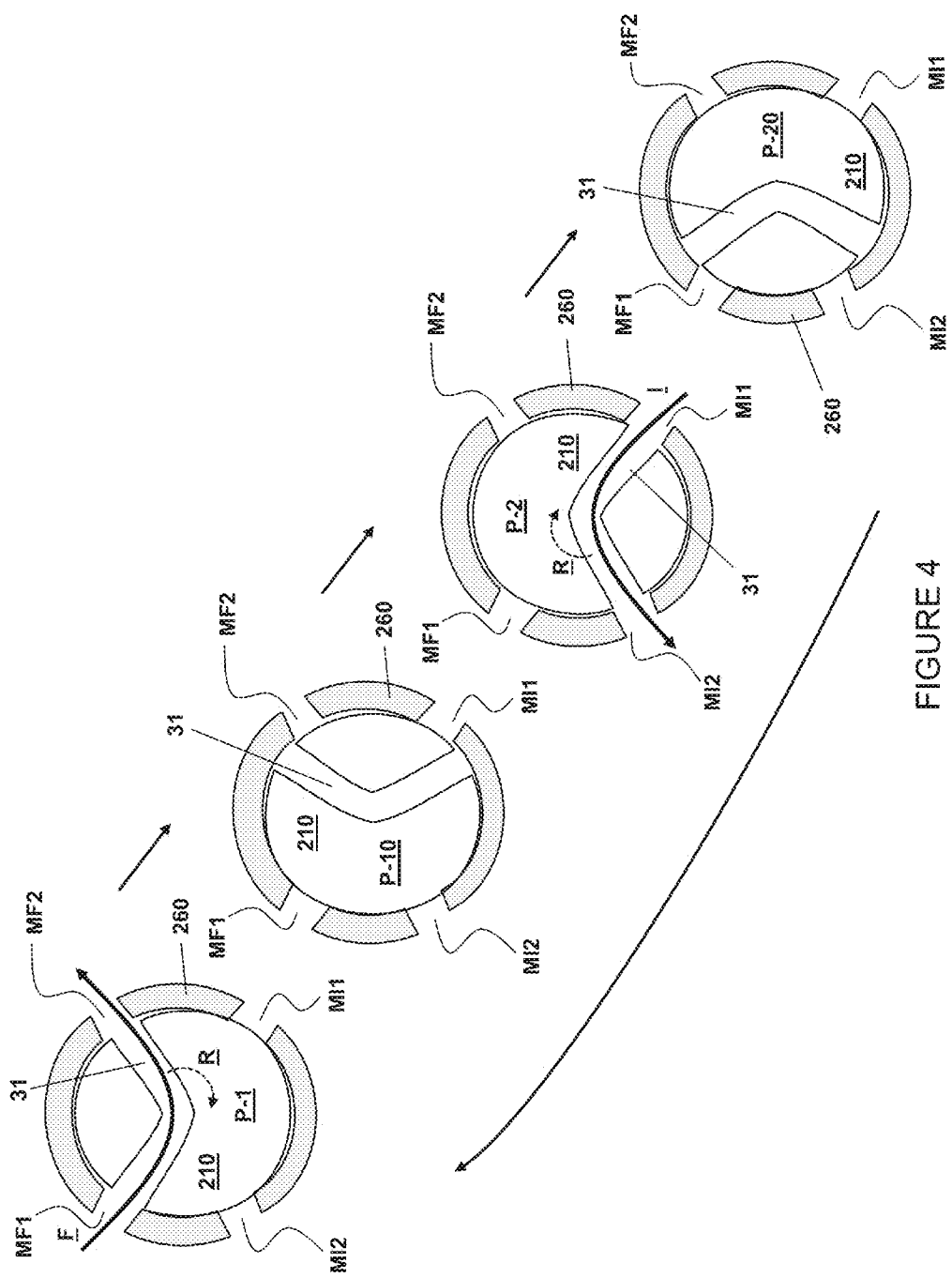
FIG. 4 is a schematic depicting operation of a manifold assembly, according to some embodiments.

With reference to FIGS. 2, 3A, and 4, each of ports MF1, MF2, MI1, and MI2 extend from a corresponding opening 362 at inner surface 36 of body 260 (two openings 362 may be seen in FIG. 3A, and the other two are shown with dashed lines in FIG. 3A) to a corresponding opening 361 at an exterior of body 260 (two openings 361 may be seen in FIG. 3A). Each port MF1, MF2, MI1, and MI2, around the corresponding external opening 361, is preferably configured with a fitting, such as a Luer fitting, for coupling with the corresponding tubing line. Alternately, each tubing line 102, 102-D, 104, 104-U may be bonded to the corresponding port of manifold assembly 25, for example, by adhesive bonding and/or ultrasonic welding methods known in the art. According to preferred embodiments of the present invention, each of internal openings 361 is located in a separate one of quadrants 1, 2, 3, 4 (FIG. 2), and flow channel 31 of core 210 is configured such that, when core 210 is rotated within body 260, about axis 10, fluid communication between fill ports MF1 and MF2 is established at a first position P-1, and fluid communication between injection ports MI1 and MI2 is established at a second position P-2, as illustrated in FIG. 4. With further reference to FIG. 4, it may be appreciated that, due to the configuration of flow channel 31, when core 210 is rotated throughout 360 degrees, for example, clockwise, per dashed-line arrow R, only the two positions, first position P-1 and second position P-2, of channel 31 conduct fluid between two of the ports of assembly 25; and, throughout the 360 degree rotation, fluid communication between any of the ports of assembly 25 is prevented, except at first and second positions P-1, P-2. According to the illustrated embodiment, rotation of core 210 from first position P-1 to second position P-2 is approximately 180 degrees.

With reference to FIG. 3B, the configuration of flow channel 31 is such that a first section, which extends inward from first opening 311, and a second section, which extends inward from second opening 312, define an angle, which is between 90 degrees and 180 degrees. FIG. 3B illustrates channel 31 defining an angle α, which is closer to 90 degrees, for example, preferably approximately 120 degrees, while a dashed line in FIG. 3B designates an angle β that channel 31 may define in an alternate embodiment, which is closer to 180 degrees. Thus, with reference, again, to FIG. 4, the configuration of flow channel 31, according to embodiments of the present invention, prevents unwanted connections between any two of ports MF1, MF2, MI1, MI2, while allowing continuous rotation of core 210 in a single direction, for example, clockwise, from position P-1 to P-2 and back to position P-1. This configuration may be compared to that of a flow channel in a prior art manifold assembly that defines a right angle and, thus, allows fluid conduction between ports that is not desired. Furthermore, the obtuse angle defined by alternate embodiments of flow channel 31 can provide for more laminar flow therethrough to mitigate entrapment of gases (e.g. air), which entrapment could be an issue for a right angle (or acute angle) flow channel.

With further reference to FIG. 2, a plane, which is designated with a vertical dashed line, extends through axes 10, 60 and divides manifold assembly 25 into two parts, such that, according to some embodiments, manifold assembly 25 is configured and integrated into system 100 so that the external portions of first fill port MF1 and second injection port MI2 are located on a fluid circuit side CS of the plane, and the external portions of second fill port MF2 and first injection port MI1 are located on a pump side PS of the plane. Furthermore, fill ports MF1, MF2 of manifold assembly 25 may be located at an elevation E1, which is higher than an elevation E2 of injection ports MI1, MI2 of assembly 25, for example, to facilitate purging of air bubbles from manifold assembly 25 and pump 130.

With reference to FIG. 3A, according to some embodiments, flow control core 210 further includes an actuation member 35 configured to engage with a drive member of the injection system that includes manifold assembly 25, for example, system 100 shown in FIG. 1. With reference to FIG. 1, reference letter D designates a general area in which a drive member, for example, a rotating shaft coupled to an electric motor, may be located. According to the embodiment illustrated in FIG. 3A, when core 210 is fitted into body 260, per arrow A, for example, with a shoulder 33 of core 210 abutting a surface 303 of body 260, actuation member 35 protrudes from a surface 305 of body 260, which is generally opposite surface 303, to be accessible for engagement with the aforementioned drive member.

FIG. 3C is another view of flow control core 210 showing actuation member 35, according to some preferred embodiments. FIG. 3C illustrates actuation member 35 having an asymmetrical shape for keyed engagement with the aforementioned drive member. Initial keyed engagement between core 210 and the drive member preferably corresponds to the illustrated locations of ports MF1, MF2, MI1 and MI2 (FIGS. 2 and 4) with flow control core 210 in either one of closed positions P10, P20 shown in FIG. 4, at which a motor encoder for the drive member may be homed at start up. With further reference to FIG. 3A, an opposite surface 34 of core 210 may include indicia formed therein that provide a visual indication of the position of core 210 relative to ports MF1, MF2, MI1 and MI2.

In the foregoing detailed description, the invention has been described with reference to specific embodiments. However, it may be appreciated that various modifications and changes can be made without departing from the scope of the invention as set forth in the appended claims.

We claim:

1. A manifold assembly for a medical injection system, the assembly comprising:
   a flow control core including a longitudinal axis, an outer perimeter surface, and a flow channel, the flow channel including a first section extending inward, toward the axis, from a first opening at the outer perimeter surface, and a second section extending inward, toward the axis, from a second opening at the outer perimeter surface; and
   a body including a longitudinal axis, an inner perimeter surface, a first fill port, a second fill port, a first injection port, and a second injection port, each port extending from a corresponding opening at the inner perimeter surface to a corresponding opening at an exterior of the body, and each port opening at the inner perimeter surface being located in a separate quadrant of four quadrants into which the inner surface is divided; and
   wherein the flow control core is fitted within the inner perimeter surface of the body such that the outer perimeter surface of the flow control core seals against the inner perimeter surface of the body, the axis of the flow control core is approximately aligned with the axis of the body, and the flow control core is rotatable about the axis thereof between a first position and a second position;
   when the flow control core is at the first position, the first opening of the flow channel aligns with the inner surface opening of the first fill port of the body, and the second opening of the flow channel aligns with the inner surface opening of the second fill port of the body, such that the channel allows fluid communication between the first and second fill ports;
   when the flow control core is at the second position, the first opening of the flow channel aligns with the inner surface opening of the first injection port of the body, and the second opening of the flow channel aligns with the inner surface opening of the second injection port of the body, such that the channel allows fluid communication between the first and second injection ports; and
   when the flow control core is rotated 360 degrees about the axis thereof, fluid communication between any ports of the body is prevented except at the first and second positions.

2. The assembly of claim 1, wherein rotation of the flow control core is approximately 180 degrees from the first position to the second position.

3. The assembly of claim 1, wherein the first and second sections of the flow channel define an angle, the angle being greater than 90 degrees and less than 180 degrees.

4. The assembly of claim 3, wherein the angle is approximately 120 degrees.

5. The assembly of claim 1, wherein the flow control core further includes an actuation member accessible from outside the body and configured to engage with a drive member of the system.

6. The assembly of claim 5, wherein the actuation member of the flow control core has an asymmetrical shape for keyed engagement with the drive member.

7. A medical injection system comprising a pump and a tubing circuit, the pump including a fill port and an injection port, and the tubing circuit including a fill tubing line coupled to a fluid reservoir and an injection tubing line; and wherein the system further comprises a manifold assembly for coupling the tubing circuit to the pump, the manifold assembly being located between the pump and tubing circuit such that the assembly has a circuit side and a pump side, opposite the circuit side; and the manifold assembly comprising:
   a flow control core including a longitudinal axis, an outer perimeter surface, and a flow channel; and
   a body including a longitudinal axis, an inner perimeter surface, a circuit side fill port, a pump side fill port, a circuit side injection port, and a pump side injection port, the fill tubing line being coupled to the circuit side fill port, the pump side fill port being coupled to the pump side fill port, the pump side injection port being coupled to the pump side injection port, and the injection tubing line being coupled to the circuit side injection port;
   wherein the flow control core is fitted within the inner perimeter surface of the body such that the outer perimeter surface of the flow control core seals against the inner perimeter surface of the body, the axis of the flow control core is approximately aligned with the axis of the body, and the flow control core is rotatable about the axis thereof between a first position, at which the flow channel of the flow control core fluidly connects the circuit side fill port to the pump side fill port, and a second position, at which the flow channel of the flow control core fluidly connects the pump side injection port to the circuit side injection port; and
   when the flow control core is rotated 360 degrees about the axis thereof, fluid communication between any ports of the body is prevented except at the first and second positions.

8. The system of claim 7, wherein rotation of the flow control core of the manifold assembly is approximately 180 degrees from the first position to the second position.

9. The system of claim 7, wherein:
   the flow channel of the flow control core of the manifold assembly includes a first section and a second section; and
   the first and second sections of the flow channel extend inward from the outer perimeter surface of the flow control core, toward one another, and define an angle, the angle being greater than 90 degrees and less than 180 degrees.

10. The system of claim 9, wherein the angle defined by the flow channel of the flow control core of the manifold assembly is approximately 120 degrees.

11. The system of claim 7, further comprising a drive member for rotating the flow control core of the manifold assembly; and wherein the flow control core further includes an actuation member accessible from outside the body and configured to engage with the drive member.

12. The system of claim 11, wherein the actuation member of the flow control core has an asymmetrical shape for keyed engagement with the drive member.

13. The system of claim 7, wherein the circuit side and pump side fill ports of the manifold assembly are located at a higher elevation than the circuit side and pump side injection ports of the manifold assembly.

* * * * *

UNITED STATES PATENT AND TRADEMARK OFFICE
CERTIFICATE OF CORRECTION

PATENT NO. : 9,067,009 B2  
APPLICATION NO. : 13/750724  
DATED : June 30, 2015  
INVENTOR(S) : David Duane Scott, Tom H. Borlaug and Scott Jacob Soltis Page 1 of 1

It is certified that error appears in the above-identified patent and that said Letters Patent is hereby corrected as shown below:

Claims

Column 6, Claim 7, line 14, the words "the pump side fill port being coupled to the pump side fill port" should be amended to "the pump side fill port being coupled to the pump's fill port." Additionally, in claim 7, starting at the end of line 14 and ending in line 15, the words "the pump side injection port being coupled to the pump side injection port" should be amended to "the pump side injection port being coupled to the pump's injection port."

Signed and Sealed this  
Twenty-seventh Day of October, 2015

Michelle K. Lee  
*Director of the United States Patent and Trademark Office*